United States Patent [19]

Chang et al.

[11] Patent Number: 5,230,916
[45] Date of Patent: Jul. 27, 1993

[54] ASCORBIC ACID COMPLEX HAVING ANTIOXIDANT FUNCTION AND IMPROVED SOLUBILITY IN LIPID MATERIALS

[75] Inventors: Stephen S. Chang, East Brunswick, N.J.; Kejian J. Wu, Clarendon Hills, Ill.

[73] Assignee: Kabi Pharmacia AB, Uppsala, Sweden

[21] Appl. No.: 813,160

[22] Filed: Dec. 23, 1991

Related U.S. Application Data

[60] Division of Ser. No. 759,499, Sep. 13, 1991, abandoned, which is a continuation-in-part of Ser. No. 638,063, Jan. 7, 1991, Pat. No. 5,077,069.

[51] Int. Cl.⁵ .......................... A23B 4/14; A23B 5/08
[52] U.S. Cl. .................................. 426/330.6; 426/72; 426/262; 426/541
[58] Field of Search ................ 426/541, 542, 330.6, 426/648, 654, 262, 268, 270, 72

[56] References Cited

U.S. PATENT DOCUMENTS

| | | | |
|---|---|---|---|
| 2,768,084 | 10/1956 | Griffith | 426/541 |
| 2,772,169 | 11/1956 | Hall | 426/541 |
| 3,852,502 | 12/1974 | Beshov | 426/542 |
| 3,852,502 | 12/1974 | Beshov | 426/544 |
| 3,950,266 | 4/1976 | Chang | 426/542 |
| 4,012,531 | 3/1977 | Viani | 426/542 |
| 4,363,823 | 12/1982 | Kimura | 426/542 |
| 4,380,506 | 4/1983 | Kimura | 426/542 |
| 4,476,112 | 10/1984 | Aversano | 426/652 |
| 4,714,571 | 12/1987 | Trembley | 426/614 |
| 4,765,927 | 8/1988 | Nomura | 426/547 |
| 4,839,187 | 6/1989 | Mai | 426/542 |
| 4,877,635 | 10/1989 | Todd | 426/542 |
| 4,925,681 | 5/1990 | Mai | 426/542 |
| 5,084,293 | 1/1992 | Todd | 426/541 |

*Primary Examiner*—Carolyn Paden
*Attorney, Agent, or Firm*—Cook, Egan, McFarron & Manzo

[57] ABSTRACT

A natural antioxidant for stabilizing polyunsaturated oils is disclosed. This oil-soluble antioxidant is prepared by dissolving ascorbic acid in a polar solvent, dissolving phospholipid in a non-polar solvent and then mixing the ascorbic acid solution with the phospholipid solution. After removing the solvent a product is formed which has anti-oxidant properties and is soluble in non-polar solvents.

14 Claims, No Drawings

ASCORBIC ACID COMPLEX HAVING ANTIOXIDANT FUNCTION AND IMPROVED SOLUBILITY IN LIPID MATERIALS

This is a divisional of copending application Ser. No. 759,499, filed on Sep. 13, 1991, now abandoned, which is a continuation-in-part of application Ser. No. 638,063, filed Jan. 7, 1991, now U.S. Pat. No. 5,077,069.

BACKGROUND OF INVENTION

The present invention relates generally to the prevention of deterioration of food, cosmetic and pharmaceutical which contain polyunsaturated fatty acids. More particularly, the present invention relates to a natural composition of antioxidants for stabilization of polyunsaturated oils comprising tocopherols, ascorbic acid, citric acid, and phospholipids. The phospholipids may be derived from soybean (commercially known as "soybean lecithin") or egg or other sources. Rosemary extract can also be added to the composition.

Today, cosmetic and pharmaceutical products containing polyunsaturated fatty acids are manufactured at plants throughout the country, prepackaged for sale, and distributed to supermarkets and convenience stores across the country. Because of the nature of such products and the transportation of such products around the country, these products require a long shelf-life. In order to increase the shelf-life, it is necessary to prevent the deterioration of the quality of the product. One cause of deterioration is oxidation. Oxidation particularly occurs with fat-containing products. For example, oils and fats containing polyunsaturated fatty acids, such as fish oils which contain eicosapentaenoic acid and decosahexaenoic acid, as well as vegetable oils which contain linoleic and/or linolenic acid, are susceptible to oxidation by oxygen in the air to form peroxides. Peroxides decompose to produce volatile compounds with objectionable odors and flavors. For example, fish oil, such as menhaden oil, can quickly develop a green, grassy and fishy odor and flavor. Soybean oil is another product which can also easily oxidize to produce the classical reversion odor and flavor. In addition, such oxidation products may be harmful to human health. Even when fish oil, such as menhaden oil, is highly purified to an odorless and flavorless oil, such as that according to the teachings of Chang et al. (U.S. Pat. No. 4,874,629), the oil can still redevelop the green and fishy odor and flavor when it is exposed to even a trace amount of air or oxygen. It has been reported that fish oil, even when packaged in gelatin capsules, can develop relatively high peroxide values during storage. Furthermore, it has been reported that tocopherols alone when added to the fish oil, even when it is packaged in gelatin capsules, cannot effectively prevent the peroxidation of the oil.

Accordingly, to use such oils in food, or as a dietary supplement, they must be stabilized to prevent or to retard the development of objectionable odors and flavors, as well as to protect the health of consumers.

Many different antioxidants and antioxidant compositions have been developed over the years. Many of these antioxidants, such as BHA and BHT, are synthetic. Today, people are more health oriented and prefer natural products which are considered safe for human consumption. In addition, synthetic compounds have recently come under heavy scrutiny by the FDA. The natural antioxidant compositions, which have been developed, also suffer from problems which limit their usefulness. For example, EP 0 326 829 (Löliger et al.) discloses a natural mixture of tocopherol, ascorbic acid, and lecithin to protect lipids against oxidation. The mixture, however, may produce a red color in the oil due to the combination of ascorbic acid and lecithin.

Accordingly, it is object of the present invention to provide a composition of natural antioxidants that will retard the oxidation of fats and oils and thus the deterioration of food products. Further, it will have improved antioxidant activity over prior compounds so as to provide better prevention of oxidation and the resulting food deterioration. In addition, the present invention will significantly decrease the undesirable color that results from the combination of ascorbic acid and lecithin in the oils or their products.

SUMMARY OF THE INVENTION

The present invention provides a composition of natural antioxidants comprising tocopherols, ascorbic acid, citric acid and phospholipids. The composition of the antioxidants of the present invention comprises from about 10% to about 62.5% by weight of tocopherols, from about 1.5% to about 20% by weight of ascorbic acid, from about 1.5% to about 20% by weight of citric acid, and from about 26% to about 85% by weight of phospholipids.

The composition preferably comprises about 29.4% tocopherols, about 5.9% ascorbic acid, about 5.9% citric acid, and about 58.8% phospholipids, all by weight.

The composition can further comprise the addition of rosemary extract as described in U.S. Pat. No. 3,950,266 to the other antioxidants listed above. With rosemary extract, the composition of the present invention comprises from about 6.5% to about 54% by weight of tocopherols, from about 1.2% to about 16% by weight of ascorbic acid, from about 1.2% to about 16% by weight of citric acid, from about 17% to about 77% by weight of phospholipids, and from about 6.5% to about 54% by weight of rosemary extract. Preferably, the composition comprises about 22.7% tocopherols, about 4.5% ascorbic acid, about 4.5% citric acid, about 45.5% phospholipids, and about 22.7% rosemary extract, all by weight.

The present invention also provides a composition of natural antioxidants for oils rich in tocopherols comprising ascorbic acid, citric acid, and phospholipids. The composition comprises from about 2% to about 27% by weight ascorbic acid, from about 2% to about 27% by weight citric acid, and from about 56% to about 95% by weight phospholipids. Preferably, the composition comprises about 8.3% ascorbic acid, 8.3% citric acid and 83.4% phospholipids, all by weight. The composition can further comprise the addition of rosemary extract to the other items listed above. With rosemary extract, the composition comprises from about 1.8% to about 23% by weight of ascorbic acid, from about 1.8% to about 23% by weight of citric acid, from about 35% to about 90% by weight of phospholipids, and from about 5% to about 45% by weight of rosemary extract. Preferably, the composition comprises about 6.9% of ascorbic acid, about 6.9% of citric acid, about 70% of phospholipids and about 17.2% of rosemary extract, all by weight.

The composition of the antioxidants of the present invention in a fish oil comprises the following percentages with relation to the oil, from about 0.05% to about 0.2% by weight of tocopherols, from about 0.01% to about 0.04% by weight of ascorbic acid, from about 0.01% to about 0.04% by weight of citric acid, and from about 0.1% to about 0.4% by weight of de-oiled soybean phospholipids. The composition can further comprise rosemary extract in an amount of from about 0.05% to about 0.2% by weight. Preferably, the composition in the fish oil comprises about 0.1% tocopherols, about 0.02% ascorbic acid, about 0.02% citric acid, about 0.2% de-oiled soybean phospholipids and about 0.1% rosemary extract, all by weight.

The composition of the antioxidants of the present invention in a tocopherols rich vegetable oil comprises the following percentages with relation to the oil from about 0.01% to about 0.04% by weight of ascorbic acid, from about 0.01% to about 0.04% by weight of citric acid, and from about 0.1% to about 0.4% by weight of de-oiled soybean phospholipids. The composition can further comprise from about 0.025% to about 0.1% by weight of rosemary extract. Preferably, the composition in the vegetable oils comprises about 0.02% ascorbic acid, about 0.02% citric acid, about 0.2% de-oiled soybean phospholipids, and about o.05% rosemary extract, all by weight.

The compositions of the present invention may be added to products containing polyunsaturated fatty acids or oils at many different concentrations, depending upon the use to which the products are to be put and the economics of the product. It has been found that the use of from about 0.10 percent to about 0.6 percent by weight, based upon the weight of the unsaturated oils produces useful results, but other concentrations may be used. In a vegetable oil that is rich in tocopherols, a composition of ascorbic acid, citric acid, phospholipids and possibly rosemary extract could be used.

DESCRIPTION OF THE PREFERRED EMBODIMENT

The present invention is concerned with a combination of natural antioxidants that together through a synergistic effect retard oxidation and the development of a green and fishy odor and flavor that results from the oxidation of polyunsaturated oils such as deodorized fish oils. A composition comprising tocopherols, ascorbic acid, citric acid, and phospholipids has been found to possess an unexpectantly effective antioxidant property.

The tocopherols used in the antioxidant compositions of the present invention generally comprise a mixture of several tocopherols isomers. Such compositions are commercially available.

The ascorbic acid and citric acid used in the antioxidant compositions of the present invention are commercially available through a variety of sources.

The phospholipids used in the antioxidant compositions of the present invention may come from various sources. While the preferred phospholipid is a de-oiled soybean phospholipid, commercially known as soybean lecithin, the phospholipids may be derived from other sources such as corn, rice, cottonseed, rapeseed, canola, and other oils.

The present invention contemplates several improvements to the phospholipids for use in the compositions of the present invention in order to provide antioxidant compositions with improved properties. The present invention contemplates the removal of carbohydrates in commercial soybean lecithin by extraction with aqueous organic solvents. The present invention also contemplates the use of a freeze drying process to dehydrate the wet gum during the preparation of soybean lecithin in order to produce a lecithin having an improved light color and less odor.

The addition of rosemary extract to the composition further enhances the composition's antioxidant property.

No single natural antioxidant, even when used at an amount equal to the total amount of the composition of the present invention, will have the same effect of antioxidant activity as that of the present composition. Further, a composition lacking any of the components of the present invention will also not have the same antioxidant activity that is achieved with the present composition.

A preferred embodiment of the composition of the present invention, especially effective for deodorized and purified fish oil such as menhaden oil, is as follows by weight:

| | |
|---|---|
| Tocopherols | 29.4% |
| Ascorbic acid | 5.9% |
| Citric acid | 5.9% |
| De-oiled soybean phospholipids | 58.8% |

The preferred amount of the above embodiment for the addition to the menhaden oil is 0.34%. The addition of 0.1% of rosemary extract by weight of the oil can further improve the effectiveness of the antioxidant activity.

Since vegetable oils are usually rich in tocopherols naturally, an example of the composition, especially effective for soybean oil is as follows by weight:

| | |
|---|---|
| Ascorbic Acid | 8.3% |
| Citric Acid | 8.3% |
| De-oiled soybean phospholipids | 83.4% |

The preferred amount of the above composition for the addition to soybean oil is 0.24% The addition of 0.05% of rosemary extract by weight of the oil can further improve the effectiveness of the antioxidant activity.

The compositions of the present invention can also be used with all omega-3 fatty acids containing oils such as menhaden oil, sardine oil, herring oil, anchovy oil, Pilchard oil, and other such oils. Other possible oils in which the present composition can retard oxidation include vegetable oils, which contain a significant amount of polyunsaturated fatty acid, such as sunflower seed oil, rapeseed oil, canola oil, corn oil, cottonseed oil, and other similar oils. Most vegetable oils already contain a sufficient amount of tocopherols naturally. Therefore, it is not necessary to add any additional tocopherols but rather to only add the other three components (and possibly rosemary extract) to achieve the synergistic effect of the present invention. Furthermore, animal fats such as lard, beef tallow, and butter can benefit by use of the composition of the present invention. Finally, other foods, cosmetic, and pharmaceutical products which contain polyunsaturated fatty acids can also have their oxidation and deterioration retarded by use of the compositions of the present invention.

EXAMPLES OF THE PRESENT INVENTION

The following examples will demonstrate that the compositions of the present invention are clearly superior in the prevention of the deterioration of products containing menhaden oil or vegetable oil than prior compositions or synthetic antioxidants.

In all of the examples, the effectiveness of the antioxidant composition is based on a determination of AOM hours (official method of American Oil Chemists' Society, Cd 12-57) using a recently developed instrument, the Rancimat (Model 617). The Rancimat was used to determine the induction period in hours at various temperatures, and at an air flow rate of 20 liters per hour.

The materials used were as follows:

Menhaden Oil: A refined and double bleached menhaden oil, supplied under the trade name of SPMO by Zapata Haynie Corporation was further deodorized at 100° C. and purified by passing through a silica gel column according to the teaching of Chang, et al. in U.S. Pat. No. 4,879,629.

Soybean Oil: A refined, bleached and deodorized soybean oil supplied by Central Soya Company Inc.

Tocopherols: Natural mixed tocopherols under the trade name of Covi-Ox T70 supplied by the Henkel Corporation.

De-oiled Soybean Phospholipids: Granular soybean lecithin containing 96% of phospholipids, under the trade name of Centrolex R, supplied by Central Soya Company, Inc.

Rosemary Extract: Standard oleoresin extract supplied by Kalsec Inc., under trade name of Herbalox® O.

EXAMPLE 1

100 g of menhaden oil was used as the control (Sample A in Table 1). Sample B was produced through the addition of 0.1 g of tocopherols dissolved in hexane, 0.02 g of ascorbic acid dissolved in anhydrous ethanol, 0.02 g of citric acid dissolved in anhydrous ethanol and 0.2 g of soybean phospholipids dissolved in hexane, to 100 g of menhaden oil. After mixing well, the solvents were removed with the use of a rotoevaporator under a vacuum and at a temperature below 80° C. Sample C was made through the addition of 0.1 g of rosemary extract, dissolved in a mixture of anhydrous ethanol and hexane (9:1 v/v), to the same formula as was previously prepared in sample B. The rosemary extract was added before the solvents were removed through the use of the rotoevaporator. The induction period for each sample was measured by the use of the rancimat. In addition, the induction period for the menhaden oil with the addition of synthetic antioxidants, BHA and BHT and for the control was also measured.

TABLE 1a

| Sample | Antioxidant Composition Added (% by weight of oil) | | Induction Period (Hours at 90° C.) |
| --- | --- | --- | --- |
| A | None | | 0.9 |
| B | Tocopherols | 0.10% | 25.2 |
|   | Ascorbic Acid | 0.02% |   |
|   | Citric Acid | 0.02% |   |
|   | Soybean Phospholipids | 0.20% |   |
| C | Tocopherols | 0.10% | 26.4 |
|   | Ascorbic Acid | 0.02% |   |
|   | Citric Acid | 0.02% |   |
|   | Soybean Phospholipids | 0.20% |   |
|   | Rosemary Extract | 0.10% |   |
| D | BHA | 0.02% | 2.1 |
| E | BHT | 0.02% | 1.7 |

Table 1a clearly shows that the induction period for the compositions of the present invention is much higher than that for Sample A which had no antioxidant added. Further, the synthetic antioxidants, at the maximum amount allowed by the FDA, have a very low induction period, not much higher than the induction period of Sample A, and considerably lower than the induction period for Samples B and C. In order to further demonstrate the antioxidant activity of the compositions, samples A, B, C, and D of Example 1 were aged at 45° for one week and for two weeks. The peroxide values of the samples, after aging is shown in Table 1b.

TABLE 1b

| Sample | Antioxidant Added (% by weight of oil) | | Peroxide Value (meq./kg.) (after aging at 45° C. for 7 or 14 days) | |
| --- | --- | --- | --- | --- |
|   |   |   | 7 days | 14 days |
| A | None | | 16.8 | 24.0 |
| B | Tocopherols | 0.10% | 0.9 | 7.9 |
|   | Ascorbic Acid | 0.02% |   |   |
|   | Citric Acid | 0.02% |   |   |
|   | Soybean Phospholipids | 0.20% |   |   |
| C | Tocopherols | 0.10% | 1.5 | 6.0 |
|   | Ascorbic Acid | 0.02% |   |   |
|   | Citric Acid | 0.02% |   |   |
|   | Soybean Phospholipids | 0.20% |   |   |
|   | Rosemary Extract | 0.10% |   |   |
| D | BHA | 0.02% | 14.3 | 23.0 |

As in the samples in Table 1a, no antioxidant has been added to Sample A, the antioxidant compositions of the present invention have been added to Samples B and C, and the synthetic antioxidant, BHA has been added to Sample D. Peroxides being the compounds which decompose to produce volatile compounds with objectionable odors and flavors, it is desirable to have a low peroxide value. Note, that Samples B and C of the present invention have a much lower peroxide value than that of the Samples A or D. Accordingly, the results of this example clearly show that the compositions of the present invention significantly retard the oxidation and the resulting deterioration of oil and do so much more effectively than a synthetic antioxidant.

EXAMPLE 2

Five samples of menhaden oil with antioxidants added were prepared in the same manner as in Example 1. The composition of Sample C of Example 1 used as the "standard" for this Example. Samples 1 through 5 were produced from the same composition as the "Standard", except that one of the five components of the composition (Sample C of Example 1) was eliminated. The induction period for each sample was then measured and compared to a composition having all five components (Standard).

TABLE 2

| Sample | Antioxidant Added | Induction Period (Hours at 90° C.) |
| --- | --- | --- |
| Control | None | 0.9 |
| Standard | Sample C of Example 1 | 26.4 |
| 1 | Elimination of Rosemary Extract | 25.2 |
| 2 | Elimination of Tocopherols | 11.8 |
| 3 | Elimination of Ascorbic Acid | 10.5 |
| 4 | Elimination of Citric Acid | 24.1 |
| 5 | Elimination of Soybean Phospholipids | 15.6 |

Table 2 clearly demonstrates that the compositions of the present invention, as represented in the Standard Sample and Sample 1, have a much higher induction period than any of the compositions having one of the components eliminated. Citric acid, as shown in Table 2, does not have a strong effect on antioxidant activity. However, it is important in the prevention of the development of an off-color.

EXAMPLE 3

The composition of Sample C of Example 1, with all five components, was used as the standard. Five samples of menhaden oil were also prepared in the same manner as in Example 1. In each sample, one of the components of the composition of the present invention (Standard) was added at a concentration of 0.44%. The induction period of each of the samples was measured.

TABLE 3

| Sample | Antioxidant Added (% by weight of oil) | Induction Period (Hours at 90° C.) |
| --- | --- | --- |
| Control | None | 0.9 |
| Standard | Sample C of Example 1 | 26.4 |
| 1 | Tocopherols, 0.44% | 2.3 |
| 2 | Ascorbic Acid, 0.44% | 1.4 |
| 3 | Citric Acid, 0.44% | 1.0 |
| 4 | De-oiled soybean phospholipids 0.44% | 1.3 |
| 5 | Rosemary extract, 0.44% | 6.9 |

Table 3 shows that each of the five components of the composition of the present invention, when added singularly, even at a concentration higher than the total amount of the five components in the Standard, does not produce an effective antioxidant activity. Thus indicating clearly that the composition of the present invention has an unusual strong antioxidant activity due to synergism.

EXAMPLE 4

The composition of the present invention has another novel advantage. The amount of phospholipids used in the present invention should be sufficient to cause the amount of ascorbic acid used in the present invention to be soluble in the oil. This makes the ascorbic acid, which is otherwise insoluble in oil, more evenly distributed into the oil and hence makes the antioxidant activity of the ascorbic acid more effective.

The unexpected but distinctive effect of phospholipids on the solubility of ascorbic acid in oils can be clearly demonstrated by the following simple example. Ten grams of ascorbic acid were dissolved in one liter of anhydrous ethanol at 60° C. and 100 grams of de-oiled soybean phospholipids [Centrolex R] were dissolved in 250 ml of hexane. The two solutions were thoroughly mixed and the solvents were then removed with the use of a rotoevaporator, under vacuum, at a temperature below 60° C. A hexane-soluble, brownish-yellow powder was obtained. It should be noticed that the ascorbic acid was originally insoluble in hexane, but after it was combined with the soybean phospholipids, the brownish-yellow powder obtained was completely soluble in hexane. This hexane solution can then be easily added into an oil such as a fish oil or vegetable oil. After the solvent is removed, a clear oil solution of ascorbic acid is obtained.

A commercial product, ascorbyl palmitate, manufactured by Hoffmann La Roche Inc. has a better oil solubility than ascorbic acid. However, the ascorbyl palmitate still cannot directly dissolve in oil. It has to be dissolved in a solvent, such as ethanol, and then dissolve the solution in oil. The ethanol will have to be removed in order to obtain a clear solution of the ascorbyl palmitate in the oil. Further, the loss of one hydroxyl group from the ascorbic acid molecule by the reaction with the palmitic acid makes the ascorbyl palmitate less effective as an antioxidant.

In order to demonstrate the above mentioned novel advantage of the present invention, another set of samples was prepared in the same manner as that described in Example 1. Samples A, B, C and D were exactly the same as described in Example 1. However, an additional sample B-PA was added. This sample (B-PA) was the same as Sample B except that the ascorbic acid was replaced by ascorbyl palmitate. Since ascorbyl palmitate has a larger molecular weight than ascorbic acid and in order for it to be equivalent to 0.02% of ascorbic acid in moles, 0.04% of ascorbyl palmitate was used.

The results of the induction period of the above mentioned samples, as shown in Table 4, clearly indicates that ascorbic acid is more effective than ascorbyl palmitate in the invented antioxidant composition.

TABLE 4

| Sample | Antioxidant Added | (% by weight of oil) | Induction Period (Hours at 90° C.) |
| --- | --- | --- | --- |
| A | None | | 0.9 |
| B | Ascorbic Acid | 0.02% | 25.2 |
| | Tocopherols | 0.10% | |
| | Citric Acid | 0.02% | |
| | Soybean Phospholipids | 0.20% | |
| B-AP | Ascorbyl Palmitate | 0.04% | 18.8 |
| | Tocopherols | 0.10% | |
| | Citric Acid | 0.02% | |
| | Soybean Phospholipids | 0.20% | |
| C | BHA | 0.02% | 2.1 |
| D | BHT | 0.02% | 1.7 |

EXAMPLE 5

The present invention is equally effective when applied to vegetable oils, such as refined, bleached, and deodorized soybean oil. Since vegetable oils are generally rich in tocopherols, no additional tocopherols were added. The samples were prepared in the same manner as those in Example 1 except that menhaden oil was replaced by refined, bleached and deodorized soybean oil.

TABLE 5

| Sample | Antioxidant Added | (by weight of oil) | Induction Period (hours at 110° C.) |
| --- | --- | --- | --- |
| A | None | | 6.50 |
| B | Ascorbic Acid | 0.02% | 13.15 |
| | Citric Acid | 0.02% | |
| | Soybean Phospholipids | 0.20% | |
| C | BHA | 0.02% | 6.50 |
| D | BHT | 0.02% | 6.60 |

Table 5 shows the induction period of these samples. The sample of the composition of the present invention (Sample B) has a much greater induction period than the synthetic antioxidants (Sample C and D) or the sample with no antioxidant (Sample A).

EXAMPLE 6

The unusual antioxidant activity of the composition of the present invention, when used in soybean oil, is demonstrated, in a manner similar to that used for menhaden oil (in Example 2), by the following results.

TABLE 6

| | Antioxidant Added (%)* | | | | Induction |
|---|---|---|---|---|---|
| Sample | Rosemary Extract | Ascorbic Acid | Citric Acid | De-oiled Soybean Phospholipids | Period (Hours at 100° C.) |
| Control | 0.00 | 0.00 | 0.00 | 0.00 | 14.6 |
| Standard** | 0.05 | 0.02 | 0.02 | 0.20 | 28.8 |
| 1 | 0.00 | 0.02 | 0.02 | 0.20 | 25.0 |
| 2 | 0.05 | 0.00 | 0.02 | 0.20 | 21.3 |
| 3 | 0.05 | 0.02 | 0.00 | 0.20 | 27.4 |
| 4 | 0.05 | 0.02 | 0.02 | 0.00 | 24.6 |

*By weight of the oil.
**A composition of the present invention.

EXAMPLE 7

This example was intended to show the superiority of the composition of the present invention over the three component composition of the prior art. The three component composition of the Löiger patent contained 0.1% tocopherol, 0.02% ascorbic acid, and 0.2% lecithin. The antioxidants from each composition were added to refined and bleached menhaden oil. In the four component composition of the present invention, 0.02% by weight citric acid was added to the components of the three component system of Löiger.

TABLE 7

| ANTIOXIDANTS ADDED* to Menhaden Oil (refined and bleached) | | | Lovibond Color (5¼" cell) | |
|---|---|---|---|---|
| | | | Red | Yellow |
| None | | | 0.6 | 10.4 |
| Ternary System as Löliger's Patent | Tocopherol | 0.10% | 3.7 | 27.7 |
| | Ascorbic Acid | 0.02% | | |
| | Lecithin | 0.20% | | |
| Four Component composition of the present invention | Tocopherol | 0.10% | 1.1 | 17.7 |
| | Ascorbic Acid | 0.02% | | |
| | Lecithin | 0.20% | | |
| | Citric Acid | 0.02% | | |

*(% by weight of oil)

Table 7 shows the difference in color between the three component composition of Löiger's patent and the four component composition of the present invention. Löiger's composition gives a much greater red color, which is undesirable, than the color resulting from the utilization of the present invention. The avoidance of the red color is considered of great importance to the quality of the oil. A difference in one unit of Lovibond color is significant. Accordingly, the compositions of the present invention, through the addition of citric acid (and rosemary extract in the five component composition), have at least three advantages over the prior art:

(1) Significantly decreases the undesirable color developed by the combination of ascorbic acid and lecithin;

(2) Has improved antioxidant activity as shown in Table 2 of Example 2, the elimination of citric acid decreases the induction period of the four component system from 26.4 to 24.1 hours; and (3) Uses a much lower amount of "Lecithin". In all the examples of Löiger's patent, 1% of "Lecithin" was used. Such a high amount of "Lecithin" will impart an undesirable odor and flavor to the product.

IMPROVED PHOSPHOLIPIDS

Commercially available vegetable phospholipids, such as the plastic soybean lecithin, contain 5% of free and bound carbohydrates, essentially plant sugars (dextrose, raffinose, galactose and stachyose). When heated to temperature above 80° C., the color of oils containing such soybean lecithin turns into dark color. This may be due to non-enzymatic browning reaction between amine-containing phospholipids, such as phosphotidyl ethanolamine and phosphotidyl serine, with carbohydrates.

Such commercial vegetable phospholipids when used in the antioxidant composition of the present invention may cause the darkening of the oil in which the antioxidant composition is added. The oil may become darker in color than the oil without the antioxidant composition. However, the amount of the soybean lecithin or phospholipids from other sources, used in the antioxidant composition are very small, and therefore, the effect of the color of the oil might be insignificant. Nevertheless, it is desirable to use a vegetable phospholipids such as soybean lecithin which have higher color stability when heated.

The present invention contemplates two methods of producing improved phospholipids from crude vegetable phospholipids, such as soybean lecithin. The product produced by these methods are hereinafter referred to as "improved phospholipids".

The first method of producing improved phospholipids involves dissolving a crude phospholipid in an organic solvent and extracting the phospholipid solution with an aqueous solution of lower alkanol, followed by removal of the solvents under vacuum at relatively low temperatures. This method yields phospholipids with improved color stability when added to oils. This method is illustrated by Examples 8 and 9, below.

A second method of producing improved phospholipids involves extracting the crude phospholipids with water, followed by freeze drying to remove the moisture. This method yields phospholipids with improved odor, flavor and color. In this method, the amount of water used for the aqueous extraction should be 2 to 5 times (W/V) of the crude phospholipid material and preferably between about 3 to 5 times (W/V). This method is illustrated by examples 10 through 14 below.

EXAMPLE 8

100 g. of plastic soybean lecithin were dissolved in 300 ml. of dimethyl ether and extracted three times with 300 ml. of an aqueous solution of 30% of isopropanol. The extractions were performed in a 2 liter separatory funnel with vigorous shaking. After the extractions, the ether layer was separated and the solvent was removed under vacuum by the use of a rotoevaporator. The product was coded as Soybean Lecithin A. Its yield was 92.5%.

EXAMPLE 9

100 g. of plastic soybean lecithin were dissolved in 400 ml. of pentane and the solution was extracted three times with 500 ml. of an aqueous solution of 60% ethanol. The extractions were performed in a 2 liter separatory funnel with vigorous shaking. In case of emulsions formed during the extraction, a few grams of sodium chloride could be used to break the emulsion. The pentane layer was separated and then freed from solvent under vacuum. The product was coded as Lecithin B. Its yield was 87.2%.

The products given in Examples 8 and 9 were analyzed by thin-layer chromatography to detect the effectiveness of the removal of carbohydrates from the commercial soybean plastic lecithin. The conditions used are as follows:

Plate: Precoated Silica Gel 60 TLC Plate, 0.25 mm. thickness.

Solvent: $CHCl_3$: $CH_3OH$:$H_2O$ = 65:25:4 v/v.

Developing: Spray with 2% $CeSO_4$ in 50% $H_2SO_4$ and heated the plate at 120° C. for 5 minutes.

The presence of carbohydrates in lecithin was indicated by the appearance of a black spot at $R_f=0$. The commercial plastic lecithin showed a dark spot at $R_f=0$ whereas both lecithin A and lecithin B showed very faint spots at $R_f=0$. This indicated that both the invented examples removed carbohydrates effectively.

The improvement of the color stability of the commercial soybean plastic lecithin by the above described novel process as described in Example 8 and Example 9 are illustrated by dissolving 2 grams of the commercial plastic lecithin, lecithin A and lecithin B in 100 grams of refined, bleached and deodorized soybean oil, respectively. The three oils each containing one of the three samples were heated to 180° C., and then cooled down.

The color of the heated oil samples was measured by Lovibond Tintometer and UV spectrophotometer. The results are shown in Table 8. It is evident that the two samples of soybean lecithin prepared according to the novel process as described in Examples 8 and 9 have distinctly improved color stability.

TABLE 8

COLOR STABILITY OF SOYBEAN OIL CONTAINING SOYBEAN LECITHIN

| Analysis | Samples | Original Soybean Oil | Heated Soybean Oil | | |
|---|---|---|---|---|---|
| | | | Soybean Oil + 2% Plastic Lecithin | Soybean Oil + 2% Plastic Lecithin A | Soybean Oil + 2% Plastic Lecithin B |
| UV Absorption (440 nm.) | | 0.220 | 4.261 | 1.340 | 1.055 |
| Lovibond | yellow | 1.1 | too high to match | 30.0 | 33.0 |
| Color | red | 0 | 33.1 | 4.1 | 5.1 |
| Measurement | gray | 0 | 7.0 | 0 | 0 |

The commercial soybean lecithin is usually prepared from the so called "Wet Gum" obtained from the refining and processing of the crude soybean oil. The wet gum is commonly dehydrated by heating under vacuum or in a falling thin film under vacuum to produce the so-called commercial soybean plastic lecithin. Since the components of wet gum are liable to heat, the dehydration process could invariably induces undesirable color and odor in the final product. The present invention is the use of freeze-drying to dehydrate the wet gum into an unexpected fluffy solid material of light color and less odor.

The present invention also contemplates washing the wet gum before freeze-drying to produce a material of even less odor. Even though a small amount of the soybean lecithin is used in the antioxidant compositions of the present invention, commercial soybean lecithin with its characteristic undesirable odor might slightly effect the quality of the oil. The phospholipids a prepared by the present novel process is more suitable for the use in the antioxidant composition of the present invention.

Even though the examples are limited to soybean phospholipids commonly called soybean lecithin, the invention can be applied to the phospholipids of other sources, such as corn oil, rice bran oil, cottonseed, canola oil and others.

The invention also contemplates the addition of starch or micronized silica such as the commercially available Cabo-Sil to the process so that a firmer product can be produced by the invented novel process.

EXAMPLE 10

A mixture of 50 grams of soybean wet gum (moisture content 33%) and 250 ml. of distilled water was blended for 3-5 minutes in a Waring Blender until a uniform emulsion was obtained. The emulsion was freeze-dried to produce 33 grams of a fluffy, light-colored solid with significantly less odor than the commercial soybean plastic lecithin produced by heat dehydration under vacuum. The moisture content of the freeze-dried product was 0.70%.

The amount of water used for the aqueous extraction should be 2 to 5 times (w/v) of the wet gum. The use of less than two times the amount of water could produce a less satisfactory product. It is preferred to use from about 3 to 5 times of the water.

EXAMPLE 11

Same as Example 10, except that 10% of starch by weight of wet gum was added to the emulsion before freeze-drying. The starch used was soluble potato starch by Sigma. The product thus obtained was firmer.

EXAMPLE 12

Same as Example 11, except 5% Cabo-Sil made by Cabot (by weight of the wet gum) was added. The product was similar to that made with 5% of starch.

EXAMPLE 13

Same as Example 11, except 5% starch was used.

EXAMPLE 14

50 grams of soybean wet gum (moisture content 33%) was mixed with 150 ml. of a 5% solution of sodium chloride in water. The mixture was blended into a uniform emulsion in a Waring Blender. The emulsion was then centrifuged and the aqueous layer separated was discarded. The gum was then washed four times with 100 ml. of 2.5% sodium chloride solution in water each time. Finally, the thick gum was made into an emulsion with 100 ml. of distilled water and 2 grams of starch. The emulsion was freeze-dried to a pale yellow fluffy solid with practically no undesirable odor.

The moisture content of the final freeze-dried product was 1.10%.

The appearance of the freeze-dried soybean lecithin according to the above-mentioned novel process is a fluffy solid practically colorless, odorless solids which is entirely different from the viscous dark brown liquid of the commercial soybean lecithin produced by the conventional process of dehydration under vacuum by heat.

The scope of the invention herein shown and described is to be considered only as illustrative. It will be apparent to those skilled in the art that numerous modifications may be made therein without departure from the spirit of the invention or the scope of the appended claims.

We claim:

1. A method of preparing an oil-soluble antioxidant composition which comprises:

dissolving an ascorbic acid in a polar solvent to form a solution thereof;
dissolving a phospholipid in a non-polar solvent to form a solution thereof;
mixing the solution of the ascorbic acid with the solution of phospholipid; and
removing solvent from said mixture to yield a product having antioxidant function which is soluble in non-polar solvents.

2. A method of preparing an oil soluble antioxidant composition which comprises:
dissolving ascorbic acid in a lower alkyl alcohol having up to three carbon atoms in the alkyl group, to from a solution thereof;
dissolving a phospholipid in a paraffinic hydrocarbon having five to eight carbon atoms in the molecule, to form a solution thereof;
mixing the solution of ascorbic acid with the solution of the phospholipid;
removing solvent from said mixture; and
recovering an ascorbic acid-phospholipid antioxidant composition having an enhanced oil solubility.

3. The method of claim 2, wherein said phospholipid is derived from a vegetable material selected from the group consisting of soybean, rice, corn, cotton seed, rapeseed, canola, and compositions thereof.

4. The method of claim 2 wherein the phospholipid is a deoiled soybean phospholipid.

5. The method as described in claim 2 wherein said lower alkyl alcohol is anhydrous ethanol.

6. The method as described in claim 2 wherein said second organic solvent is hexane.

7. The method as described in claim 2 wherein the weight ratio of ascorbic acid to phospholipid is between 1 to 1.5 and 1 to 60.

8. The method of claim 2 wherein said ascorbic acid-phospholipid composition is combined with other antioxidant components.

9. The method of claim 2 wherein said ascorbic acid-phospholipid composition is combined with an antioxidant selected from the group consisting of citric acid, tocopherols, rosemary extract, and mixtures thereof.

10. The method of claim 2 wherein said solvents are completely removed from said mixture and a dry ascorbic acid-phospholipid composition is recovered.

11. An oil-soluble antioxidant composition produced by the process of
dissolving an ascorbic acid in a polar solvent to form a solution thereof;
dissolving a phospholipid in a non-polar solvent to form a solution thereof;
mixing the solution of the ascorbic acid with the solution of phospholipid; and
removing solvent from said mixture to yield a product having antioxidant function which is soluble in non-polar solvents.

12. An oil soluble antioxidant composition having enhanced oil solubility, said composition produced by the process of:
dissolving ascorbic acid in a lower alkyl alcohol having up to three carbon atoms in the alkyl group, to from a solution thereof;
dissolving a phospholipid in a paraffinic hydrocarbon having five to eight carbon atoms in the molecule, to form a solution thereof;
mixing the solution of ascorbic acid with the solution of the phospholipid;
removing solvent from said mixture; and
recovering an ascorbic acid-phospholipid antioxidant composition having an enhanced oil solubility.

13. A method of preparing an ascorbic acid complex having improved solubility in lipid materials which comprises:
dissolving an ascorbic acid in a polar solvent to form a solution thereof;
dissolving a phospholipid in a non-polar solvent to form a solution thereof;
mixing the solution of the ascorbic acid with the solution of phospholipid; and
removing solvent from said mixture to yield an ascorbic acid complex having antioxidant function and having improved solubility in lipid materials.

14. An ascorbic acid complex having improved solubility in lipid materials produced by the process of:
dissolving an ascorbic acid in a polar solvent to form a solution thereof;
dissolving a phospholipid in a non-polar solvent to form a solution thereof;
mixing the solution of the ascorbic acid with the solution of phospholipid; and
removing solvent from said mixture to yield an ascorbic acid complex having antioxidant function and having improved solubility in lipid materials.

* * * * *

UNITED STATES PATENT AND TRADEMARK OFFICE
CERTIFICATE OF CORRECTION

PATENT NO. : 5,230,916
DATED : July 27, 1993
INVENTOR(S) : Stephen S. Chang, Kejian J. Wu It is certified that error appears in the above-indentified patent and that said Letters Patent is hereby corrected as shown below:

Column 9, line 20; "Löiger" should read -- Löliger --
Column 9, line 26; "Löiger" should read -- Löliger --
Column 9, line 41; "Löiger's" should read -- Löliger's --
Column 9, line 42; "Löi-" should read -- Löli- --

Signed and Sealed this

Tenth Day of January, 1995

Attest:

BRUCE LEHMAN

Attesting Officer     Commissioner of Patents and Trademarks